(12) United States Patent
DeToro et al.

(10) Patent No.: US 7,846,120 B2
(45) Date of Patent: Dec. 7, 2010

(54) ORTHOTIC DEVICE HAVING COUPLING SEGMENTS

(75) Inventors: William W. DeToro, Poland, OH (US);
Brian S. Perala, Warren, OH (US);
William A. DeToro, Poland, OH (US);
Jack N. Huey, Poland, OH (US)

(73) Assignee: Anatomical Concepts, Inc., Poland, OH (US)

( * ) Notice: Subject to any disclaimer, the term of this patent is extended or adjusted under 35 U.S.C. 154(b) by 281 days.

(21) Appl. No.: 12/221,474

(22) Filed: Aug. 1, 2008

(65) Prior Publication Data

US 2010/0030123 A1 Feb. 4, 2010

(51) Int. Cl.
*A61F 5/00* (2006.01)
*A61F 5/37* (2006.01)

(52) U.S. Cl. .......................... 602/28; 128/882
(58) Field of Classification Search .............. 602/5, 602/16, 23, 25–26, 27; 128/882
See application file for complete search history.

(56) References Cited

U.S. PATENT DOCUMENTS

| | | | |
|---|---|---|---|
| 649,237 A | 5/1900 | Dyson | |
| 2,413,634 A | 12/1946 | Kolarik | |
| 2,558,986 A | 7/1951 | Seelert | |
| 2,578,108 A * | 12/1951 | Thornton | 602/16 |
| 3,827,431 A | 8/1974 | Pecorella | |
| 3,844,279 A | 10/1974 | Konvalin | |
| 4,379,463 A | 4/1983 | Meier et al. | |
| 4,564,365 A | 1/1986 | Winer et al. | |
| 5,078,128 A | 1/1992 | Grim et al. | |
| 5,116,382 A | 5/1992 | Steinkamp et al. | |
| 5,368,551 A | 11/1994 | Zuckerman | |
| 5,429,588 A | 7/1995 | Young et al. | |
| 5,545,127 A | 8/1996 | DeToro | |
| 5,593,383 A | 1/1997 | DeToro | |
| 5,681,267 A | 10/1997 | Molino et al. | |
| 5,851,194 A | 12/1998 | Fratrick | |
| 6,129,689 A | 10/2000 | Dibello | |
| 6,302,858 B1 | 10/2001 | DeToro et al. | |
| 6,350,246 B1 | 2/2002 | DeToro et al. | |
| 6,736,567 B1 | 5/2004 | Dibello | |
| 7,011,641 B1 | 3/2006 | DeToro et al. | |
| 7,122,016 B1 | 10/2006 | DeToro et al. | |
| 7,147,612 B2 | 12/2006 | Molina et al. | |
| 2002/0169402 A1* | 11/2002 | Hatton et al. | 602/26 |
| 2006/0293624 A1* | 12/2006 | Enzerink et al. | 602/23 |
| 2007/0027421 A1* | 2/2007 | Nobbe et al. | 602/27 |
| 2009/0030353 A1* | 1/2009 | Bonutti et al. | 601/5 |

* cited by examiner

*Primary Examiner*—Patricia M Bianco
*Assistant Examiner*—Tarla R Patel
(74) *Attorney, Agent, or Firm*—Robert J. Herberger (57) ABSTRACT

An orthotic device for supporting a jointed limb of the human body includes a first segment having a first support member that extends along a posterior portion of the limb about the joint, a first support pad secured to the first support member, and a channel slot extending along the first support member. An extension segment includes a second support member that also extends along the posterior portion of the limb and a second support pad secured to the second support member. The second support member can be adjustably coupled to the first segment by entering and engaging the channel slot.

12 Claims, 9 Drawing Sheets

ORTHOTIC DEVICE HAVING COUPLING SEGMENTS

BACKGROUND OF THE INVENTION

1. Field of the Invention

This invention relates generally to an orthotic device, and particularly to an orthotic that can be adapted to selectively support various portions of a jointed limb of the human body.

2. Description of the Prior Art

An orthotic is a device, such as a brace or splint, for supporting, immobilizing, or treating muscles, joints, or skeletal parts that are weak, ineffective, deformed, or injured.

A patient, such as a stroke patient who is at least partially physically impaired, may require a brace to support and stabilize the ankle. The brace usually includes an ankle and foot support that extends from the underside of the foot, around the back of the ankle and upward to the lower portion of the calf. The ankle and foot support is usually removed before entering bed and while the patient is in bed.

When the patient is to walk or attend a session in which physical therapy is administered, the patient's leg must often be supported along a greater length than that of the foot support, e.g., from the upper portion of the calf, across the knee joint to the thigh. To provide this enhanced support to the leg, it is conventional to remove the foot brace and to replace it with a longer brace that extends from the underside of the foot, around the back of the ankle, along the calf, possibly to the thigh. Due to the size of the replacement brace, the patient's weakened physical condition, lack of stamina and partial paralysis on the affected side of the body that requires the brace, the patient needs assistance in removing the foot brace and securing the longer brace to the patient's leg.

A need exists for an orthotic device comprising various length segments that can be readily connected to and disconnected from a short brace, thereby increasing its length and the length of the leg or arm that is supported by the brace. Preferably the orthotic device is easily assembled in segments so that it can be quickly disassembled and restored to its shorter length when need for the greater length of support is past.

SUMMARY OF THE INVENTION

An orthotic device for supporting a limb of the human body includes a first segment (such as an ankle and foot segment) including a first support member that extends along a posterior portion of the jointed limb, a first support pad secured to the first support member, and a channel slot extending along the posterior portion of the limb and secured to the first support member. An extension segment (such as an upper calf extension segment to further support the calf or a leg extension segment to support the thigh and knee) includes a second support member that also extends along the posterior portion of the limb and a second support pad secured to the second support member. The second support member is easily coupled to the first segment by entering and engaging the slot.

Adjustment screws located in the slot and engaging the second support member and the slot, can be used to adjust an angular disposition of the second support member with respect to a reference axis. Shims or inclined inner surfaces on the walls of the slot with respect to the reference axis can be used to provide a desired angular disposition of the support member with respect to the reference axis.

The orthotic is manufactured from lightweight structural material, e.g., plastic and aluminum, which is formed by conventional techniques and at low cost. Angular adjustability of the first segment (i.e. ankle and foot segment) of the orthotic with respect to a longitudinal reference axis and the extension segment (e.g. leg extension segment supporting the upper calf, knee and thigh), which is spaced along a jointed limb, produces some additional advantages, including the ability to easily and quickly adjust the first segment relative to the second segment to accommodate and urge correction of anomalies associated with soft tissue injuries about the joint (commonly the knee).

The scope of applicability of the preferred embodiment will become apparent from the following detailed description, claims and drawings. It should be understood, that the description and specific examples, although indicating preferred embodiments of the invention, are given by way of illustration only. Various changes and modifications to the described embodiments and examples will become apparent to those skilled in the art.

DESCRIPTION OF THE DRAWINGS

Having generally described the nature of the invention, reference will now be made to the accompanying drawings used to illustrate and describe the preferred embodiments thereof. Further, these and other advantages will become apparent to those skilled in the art from the following detailed description of the embodiments when considered in the light of these drawings in which.

DESCRIPTION OF THE PREFERRED EMBODIMENT

Figure 1:
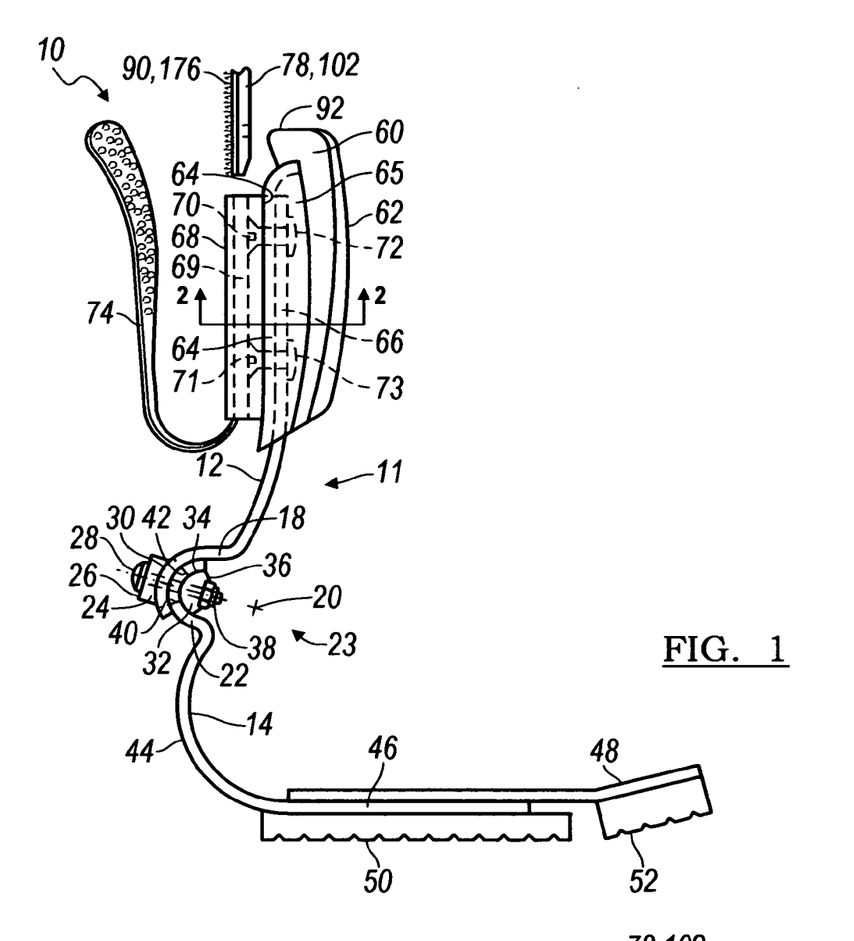
FIG. 1 is a side elevational view of an ankle and foot segment of an orthotic device.
Figure 2:
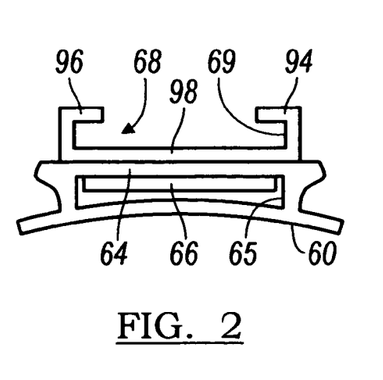
FIG. 2 is a cross section taken at plane 2-2 of FIG. 1 showing a bracket slot used to extend the ankle and foot segment.
Figure 3:
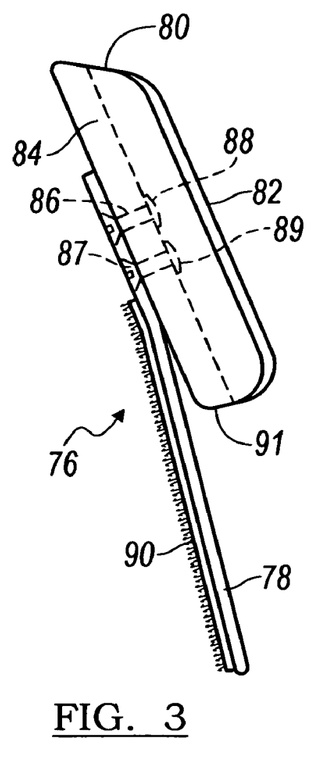
FIG. 3 is side view of a first extension segment, i.e. an upper calf support extension segment that can be coupled to the ankle and foot segment of FIG. 1.

Referring now to FIGS. 1 through 3, an ankle and foot segment 11 or first segment of an orthotic 10 includes ankle and foot support members 12 and 14, respectively, each support member preferably being a bar of aluminum or another structural material having density, strength and endurance comparable to those of aluminum.

The lower end of the ankle support member 12 is formed with a circular arc 18 having a center 20. The upper end of the foot support member 14 is formed with a circular arc 22, which is centered at 20 and whose outer surface nests within the inner surface of arc 18. The ankle and foot support members 12 and 14 are connected mutually at an adjustable connection 23. An outer block 24 is formed with a flat outer surface 26, engaged by the head of threaded attachment 28, e.g., a screw or bolt, and a circular cylindrical inner surface 30 centered at 20. An inner block 32 is formed with a circular cylindrical outer surface 34 centered at 20, and a flat inner surface 36 contacted by laterally spaced self-locking nuts 38, each nut engaging a respective attachment 28. Support member 12 is formed with two parallel slotted holes 40. The ankle support member 14 is formed with two slotted holes 42, each hole 42 being aligned with a respective hole 40. Each attachment 28 extends through a hole in the outer block 24, paired holes 40, 42 in members 12 and 14, and a hole in the inner block 32.

In operation, the angular disposition of the ankle and foot connection 23 is adjusted by loosing the engagement of nuts 38 with screw attachments 28 sufficiently to permit the arcuate surfaces 18, 22 of members 12, 14 to rotate about center 20 as the slotted holes 40, 42 slide relative the attachments. When the desired angular position is established, the nuts 38 are retightened with screw attachments 28, which draws blocks 24, 32 and the arcuate surfaces 18, 22 of members 12, 14 into friction contact and secures the desired angular setting of the ankle and foot connection 23.

Figure 8:
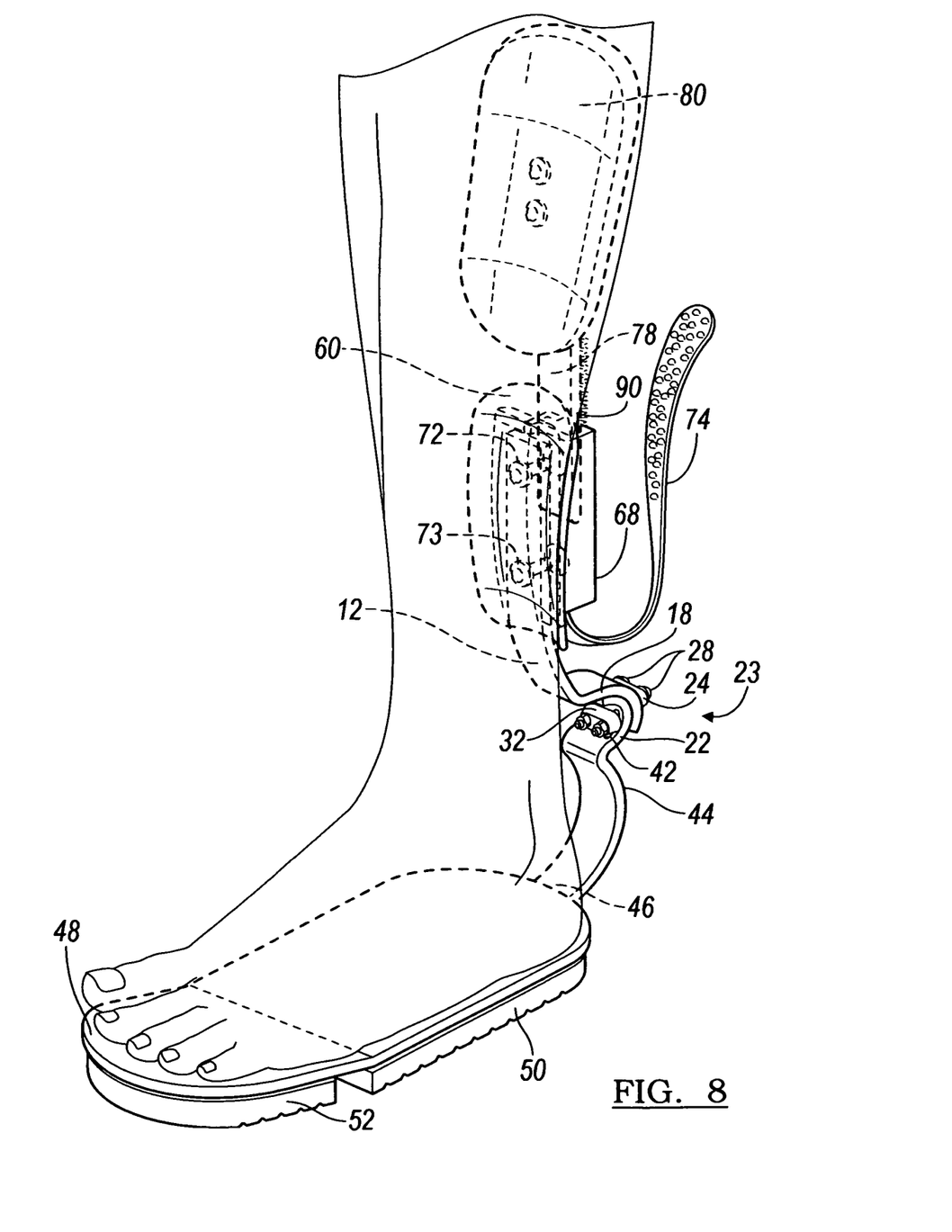
FIG. 8 is a perspective view showing the orthotic device of FIG. 6 positioned to support a leg.
Figure 9:
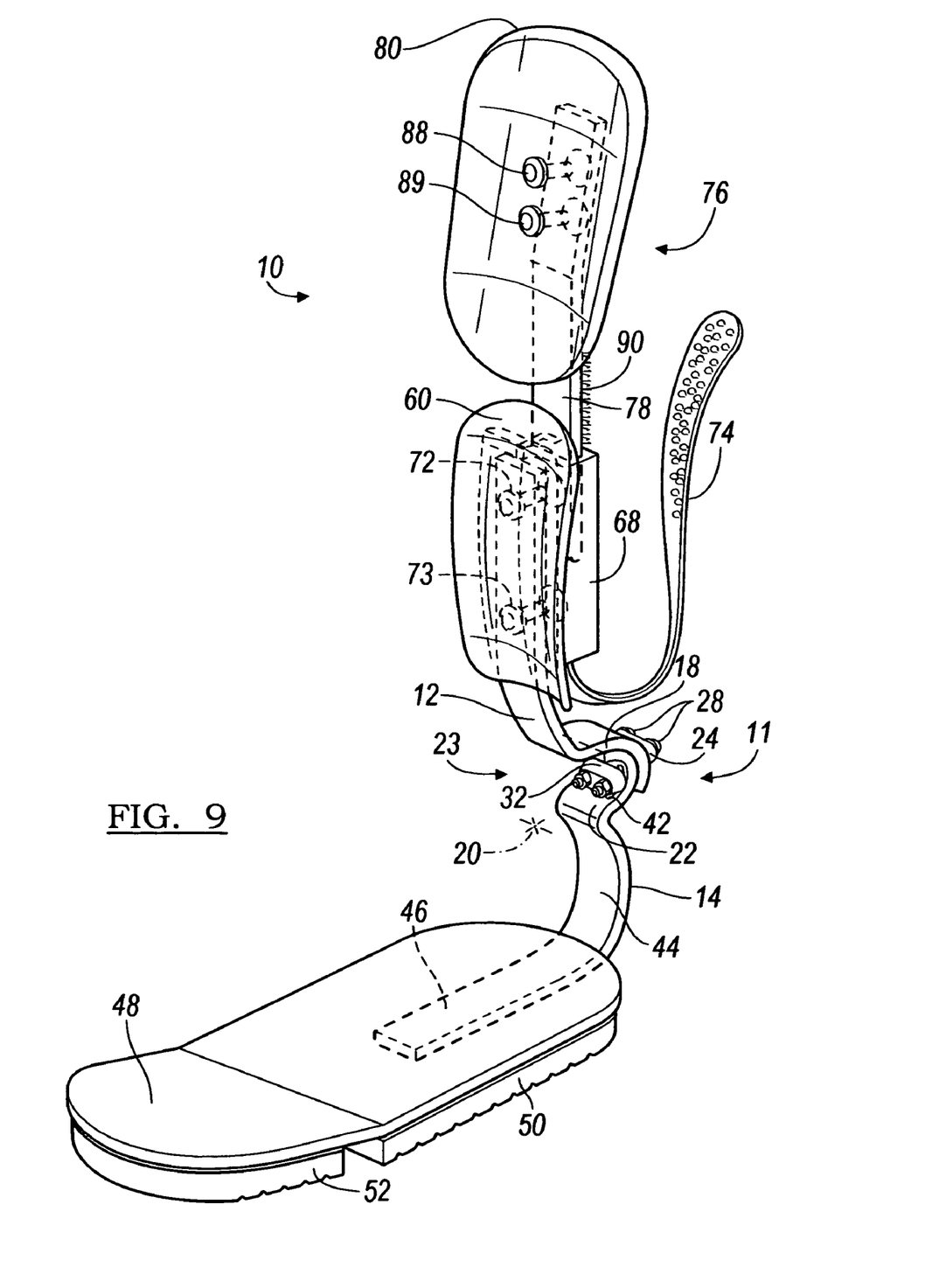
FIG. 9 is a perspective view of the orthotic device of FIG. 6.

The lower portion of foot support member 14 is formed with an arc 44 (to suspend the heel) and a flat surface 46 to support a foot pad extending forward from the arc. The foot pad having a toe support surface 48 being inclined upward from a horizontal plane. The arc 44 and surfaces 46, 48 extend along the lower surface of a human foot, and around the heel and ankle, as FIG. 8 illustrates. Walking bases 50, 52, preferably of rubber, are attached to the underside of the foot member 14 to resist slippage.

The upper end of the ankle support member 12 carries a lower calf support pad 60, which includes a front surface 62, a portion of whose contour conforms to that of the lower calf of the human leg. The lower calf support pad 60 includes a rear wall 64, formed with an inner channel 65, which extends along the calf of the user's leg. Channel 65 has a length that extends along the lower calf support pad 60 and a width that is able to accept the upper portion 66 of the ankle support member 12.

A bracket 68 is formed with a channel slot 69 and is secured by upper and lower countersunk screws 70, 71, each of which passes through the bracket 68, the rear wall 64 of the lower calf support pad 60, and the upper portion 66 of the ankle support member 12. Each screw 70, 71 is engaged with a respective nut 72, 73.

A strap of velcro 74 is secured to the lower calf support pad 60 at the inner channel 65 and has a length that extends upward past the end of the channel. The width of the velcro strap 74 is about the same as the distance between flanges 94, 96 of the bracket 68, shown in FIGS. 2 and 4.

FIG. 3 illustrates an extension segment (in this case, an upper calf support extension segment 76) of the orthotic device 10 comprising an upper calf support member 78, which is preferably of aluminum having a length that extends along the calf above the location of lower calf support pad 60, and a width that is able to fit within the slot 69 of bracket 68. The upper end of the upper calf support member 78 carries an upper calf support pad 80, which includes a front surface 82, whose contour conforms to a portion of the convex contour of the middle-to-upper calf of the human leg, i.e. above the lower calf support pad 60. The upper calf support pad 80 includes a rear wall 84, to which the support pad is secured by upper and lower countersunk screws 86, 87, each of which passes through the rear wall 84 of support pad 80 and the upper portion of the upper calf support member 78. Each screw 86, 87 is engaged with a respective nut 88, 89. A strip of velcro 90 is bonded to the back surface of upper calf support member 78.

Figure 6:
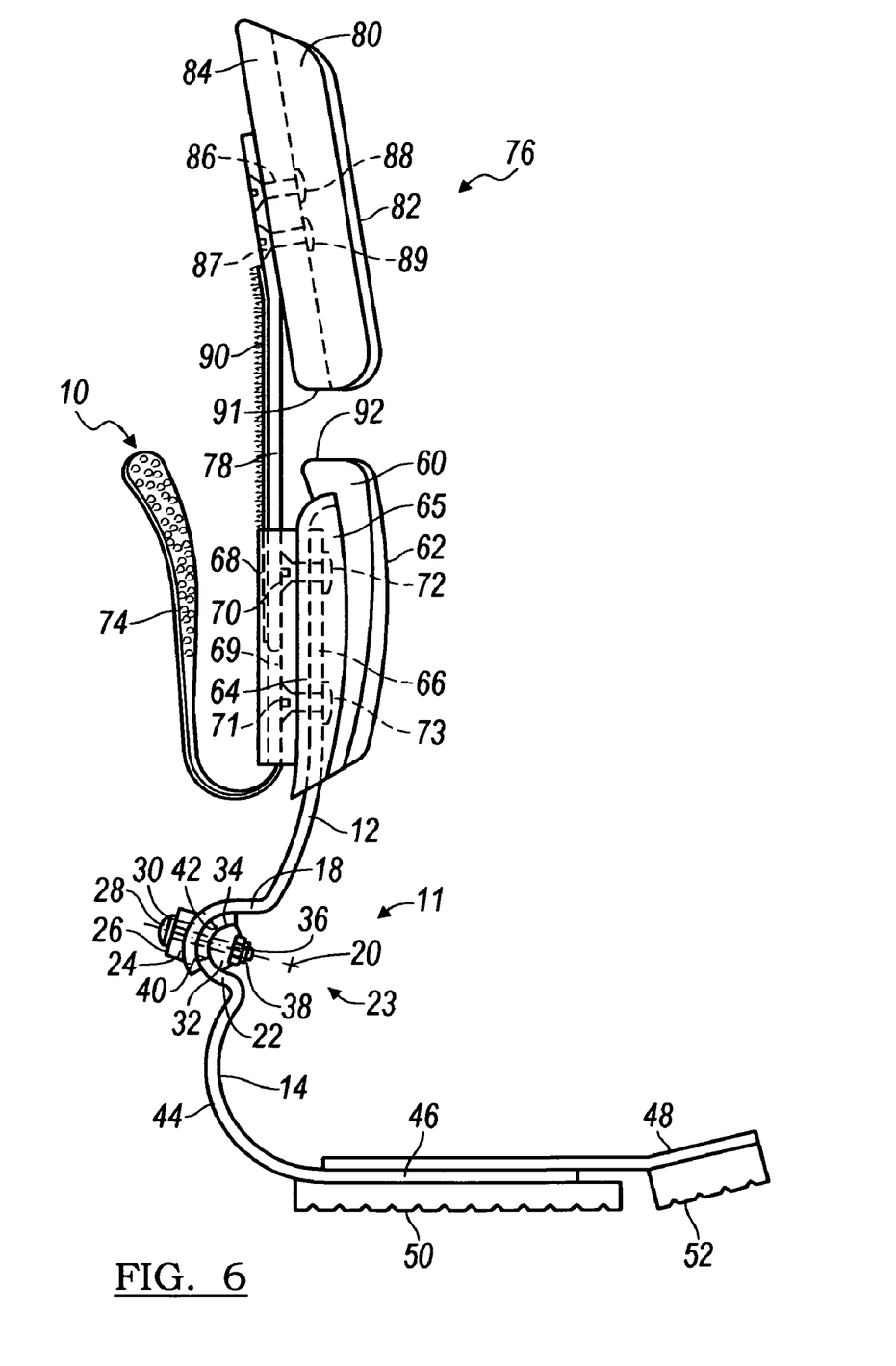
FIG. 6 is a side elevational view showing the upper calf support extension segment of FIG. 3 partially inserted into the ankle and foot segment of FIG. 1.

In operation, the length of support along the calf that is provided by lower calf support pad 60 is increased by sliding the lower end of the upper calf support member 78 into the longitudinal channel slot 69 of bracket 68, as FIGS. 4, 6, 8 and 9 illustrate. Contact between the lower surface 91 of the upper calf support pad 80 and the upper surface 92 of the lower calf support pad 60 limits the extent to which the support member 78 can enter the channel slot 69. As FIG. 6 illustrates, with the orthotic 10 in this position, the combined front surfaces 62, 82 of support pads 60, 80, respectively, provide surfaces that support the calf. After support member 78 is inserted into the slot 69 of bracket 68, velcro strap 74 is lapped over strip 90, thereby releasably securing the upper calf support extension segment 76 to the ankle and foot segment 11.

Figure 4:
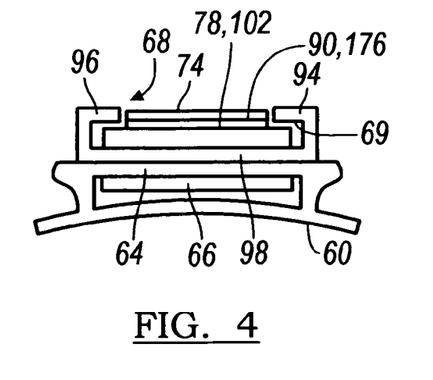
FIG. 4 is a cross section taken at plane 2-2 of FIG. 2 showing a support member of an extension segment located in and engaged with a bracket slot.

As FIG. 4 shows, the upper calf support member 78 (or the alternative upper leg support member 102 described subsequent in more detail) is restrained within longitudinal channel slot 69 against posterior and anterior movement due to its contact with the rear surfaces of the laterally spaced flanges 94, 96 of bracket 68 and the front wall 98 of the bracket. Downward movement of support member 78 is restrained within slot 69 by contact between surfaces 91, 92. But support member 78 can be moved upward to remove it from slot 69, thereby restoring orthotic 10 to the ankle and foot support shown in FIG. 1.

Figure 5:
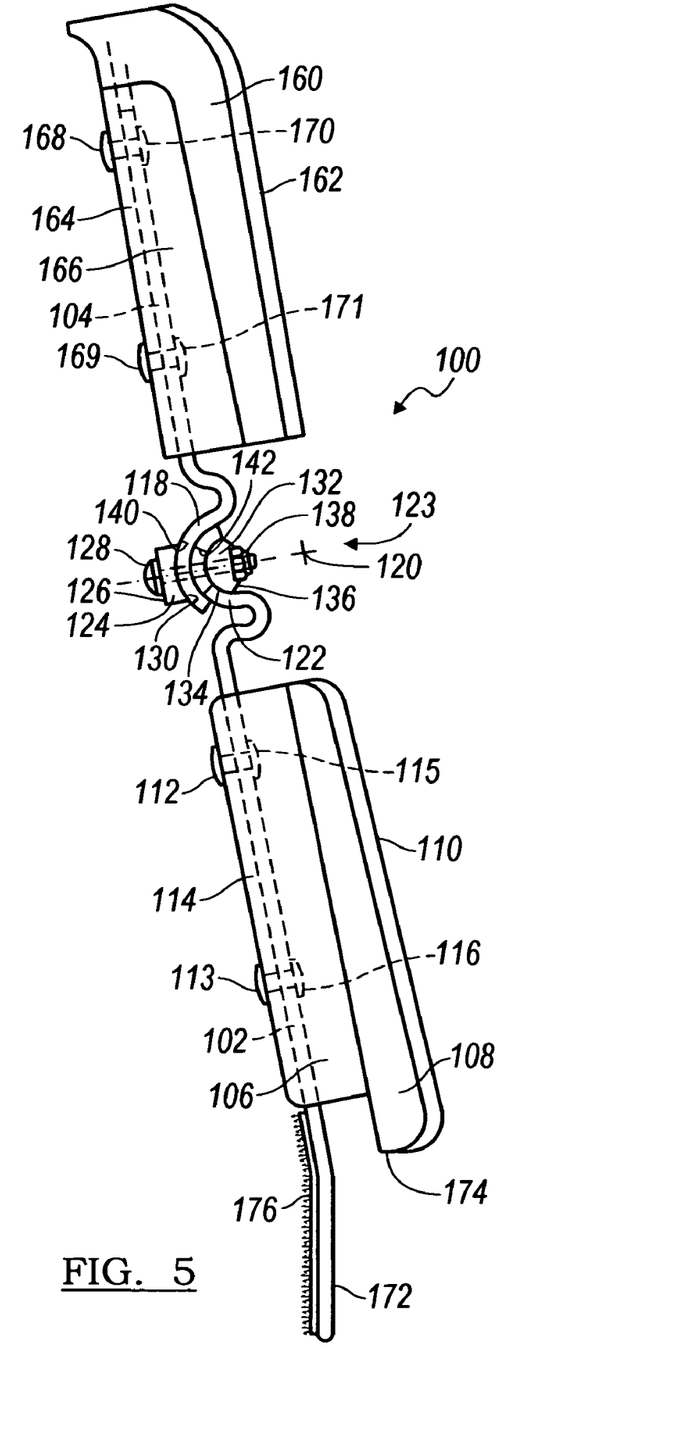
FIG. 5 is a side view of a second extension segment, i.e. a leg extension segment to support the upper calf, knee and thigh, that can be coupled to the ankle and foot segment of FIG. 1.

FIG. 5 illustrates an alternative extension segment, i.e. leg extension segment 100 for the upper leg, that combines a below-knee extension upright with an above-knee or thigh upright of the orthotic device 10. The leg extension segment 100 comprising a lower leg support member 102 and a thigh support member 104, each member being preferably of aluminum. The lower leg support member 102 has a length that extends along the back of the calf above the location of lower calf support pad 60, and a width that fits within a channel 106 formed in a lower leg support pad 108 and in the channel slot 69 of bracket 68. The lower leg support pad 108 includes a front surface 110, a portion of whose contour conforms to that of the upper calf of a leg, much like that of the upper calf support pad 80 described above.

The lower leg support pad 108 is secured to the lower leg support member 102 by upper and lower screws 112, 113, each of which passes through the rear wall 114 of the lower leg support pad 108 and the thickness of the lower leg member 102. Each screw 112, 113 is engaged with a respective nut 115, 116.

The lower end of the upper leg support member 104 is formed with a circular arc 118 having a center 120. The upper end of the lower leg support member 102 is formed with a circular arc 122, which is centered at 120 and whose outer surface nests within the inner surface of arc 118. Leg support members 102 and 104 are connected mutually at an adjustable knee connection 123. An outer block 124 is formed with a flat outer surface 126, engaged by the head of threaded attachment 128, e.g., a screw or bolt, and a circular cylindrical inner surface 130 centered at 120. An inner block 132 is formed with a circular cylindrical outer surface 134 centered at 120, and a flat inner surface 136 contacted by laterally spaced self-locking nuts 138, each nut engaging a respective attachment 128. The arc 118 of the upper leg support member 104 is formed with two parallel slotted holes 140. The arc 122 of the third support member 102 is formed with two slotted holes 142, each hole 142 being aligned with a respective hole 140. Each attachment 128 extends through a hole in the outer block 124, paired holes 140, 142 in support member 104 and 102, respectively, and a hole in the inner block 132.

In operation, the angular disposition of the knee connection 123 is adjusted by loosing the engagement of nuts 138 with screws 128 sufficiently to permit the arcuate surfaces 118, 122 of support member 102, 104 to rotate about center 120 as the slotted holes 140, 142 slide relative the attachments. When the desired angular position is established, the nuts 138 are retightened with screw attachments 128, which draws blocks 124, 132 and the arcs 118, 122 of support member 104, 102 into friction contact and secures the desired angular setting of the upper leg support member 104 relative to the lower leg support member 102 at the knee connection 123.

The upper leg support member 104 carries a thigh support pad 160, which includes a front surface 162, a portion of whose contour conforms to the contour of the back of the thigh of the human leg. The support pad 160 includes a rear wall 164, formed with a channel 166, which has a length that extends along the thigh support pad 160 and a width that is able to accept the width of the upper leg support member 104. The thigh support pad 160 is secured to the upper leg support member 104 by upper and lower screws 168, 169, each of which passes through the rear wall 164 of the thigh support pad 160 and the thickness of the upper leg support member 104. Each screw 168, 169 is engaged with a respective nut 170, 171.

Figure 7:
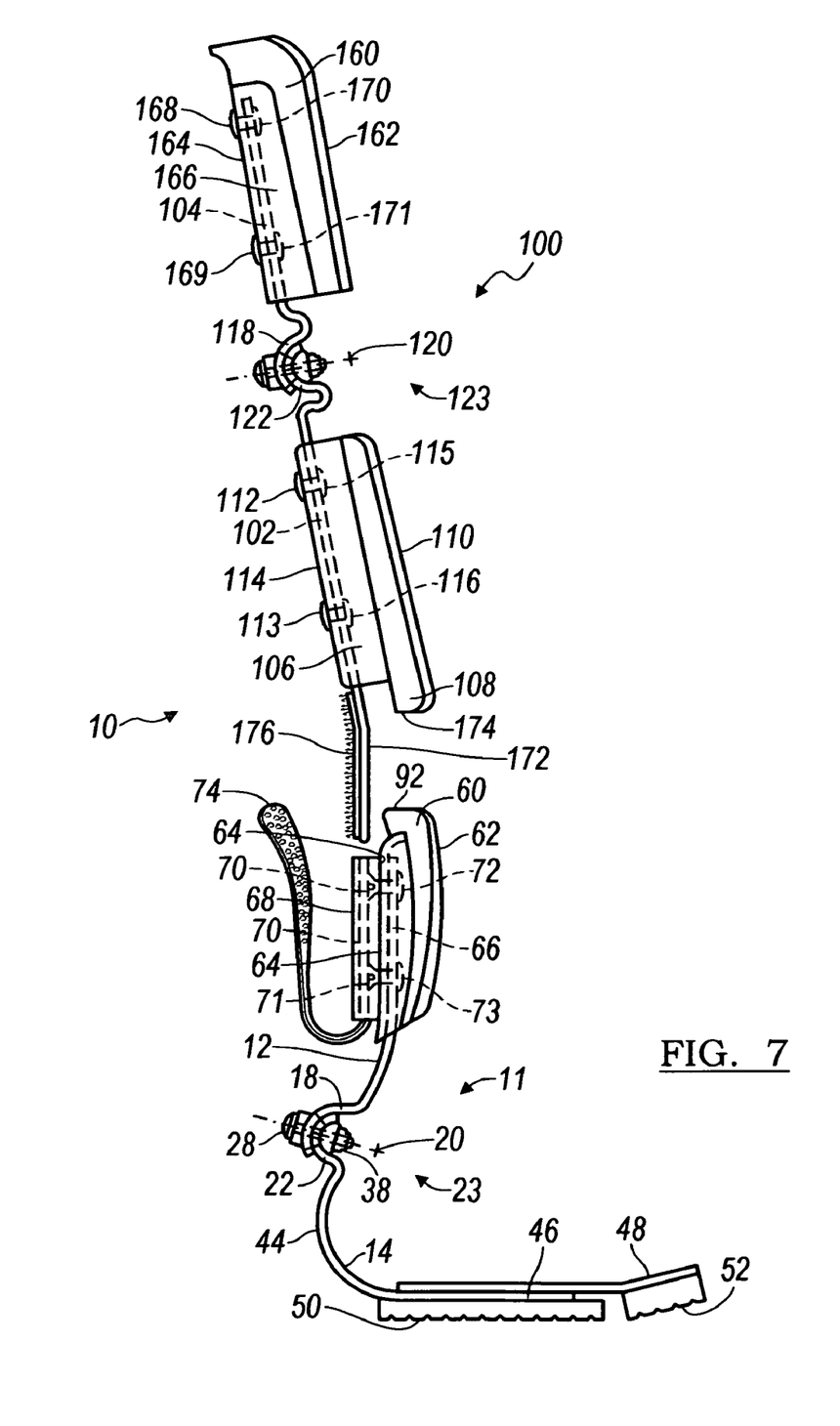
FIG. 7 is a side elevational view showing the leg extension segment of FIG. 5 in position to be inserted into the ankle and foot segment of FIG. 1.

In operation, the length of support along the calf that is provided by the lower calf support pad 60 of the ankle and foot segment 11 of orthotic 10 is increased by sliding the lower end 172 of the lower leg support member 102 into the longitudinal slot 69 of bracket 68, as shown in FIG. 7. Contact between the lower surface 174 of lower leg support pad 108 and the upper surface 92 of the lower calf support pad 60 limits the extent to which the lower leg support member 102 can enter the longitudinal slot 69. With the orthotic 10 in this position, the combined surfaces 62, 110 of support pads 60, 108, respectively, support the calf, and the surface 162 of the thigh support pad 160 supports the back of the thigh. Notably, a strip of velcro 176 is bonded to the surface of the lower end 172 of the lower leg support member 102. After lower leg support member 102 is inserted into the slot 69 of bracket 68, velcro strap 74 is lapped over velcro strip 176, thereby releasably securing the leg extension segment 100 to the ankle and foot segment 11.

As previously described above with reference to FIG. 4, the lower leg support member 102, like the upper calf support member 78, is restrained within longitudinal channel slot 69 against posterior and anterior movement due to its contact with the rear surfaces of the laterally spaced flanges 94, 96 of bracket 68 and the front wall 98 of the bracket. Downward movement of the lower leg support member 102 is restrained within slot 69 by contact between surfaces 92, 174. Also, the lower leg support member can be moved upward to remove it from slot 69, thereby restoring the orthotic 10 to the ankle and foot segment 11 shown in FIG. 1.

Figure 10:
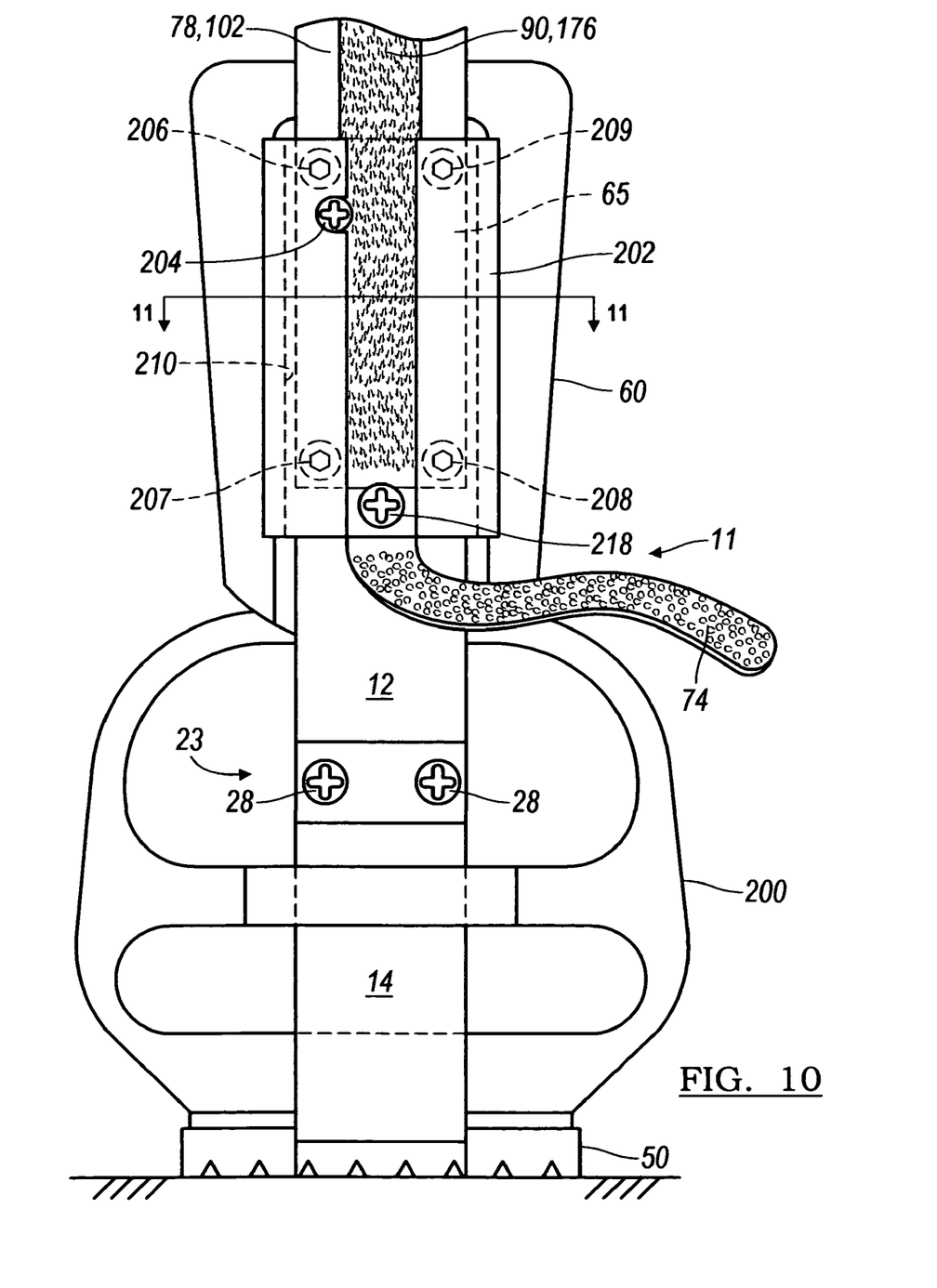
FIG. 10 is a rear view of the ankle and foot segment adapted to include an angularly adjustable support member of one of the extension segments.
Figure 11:
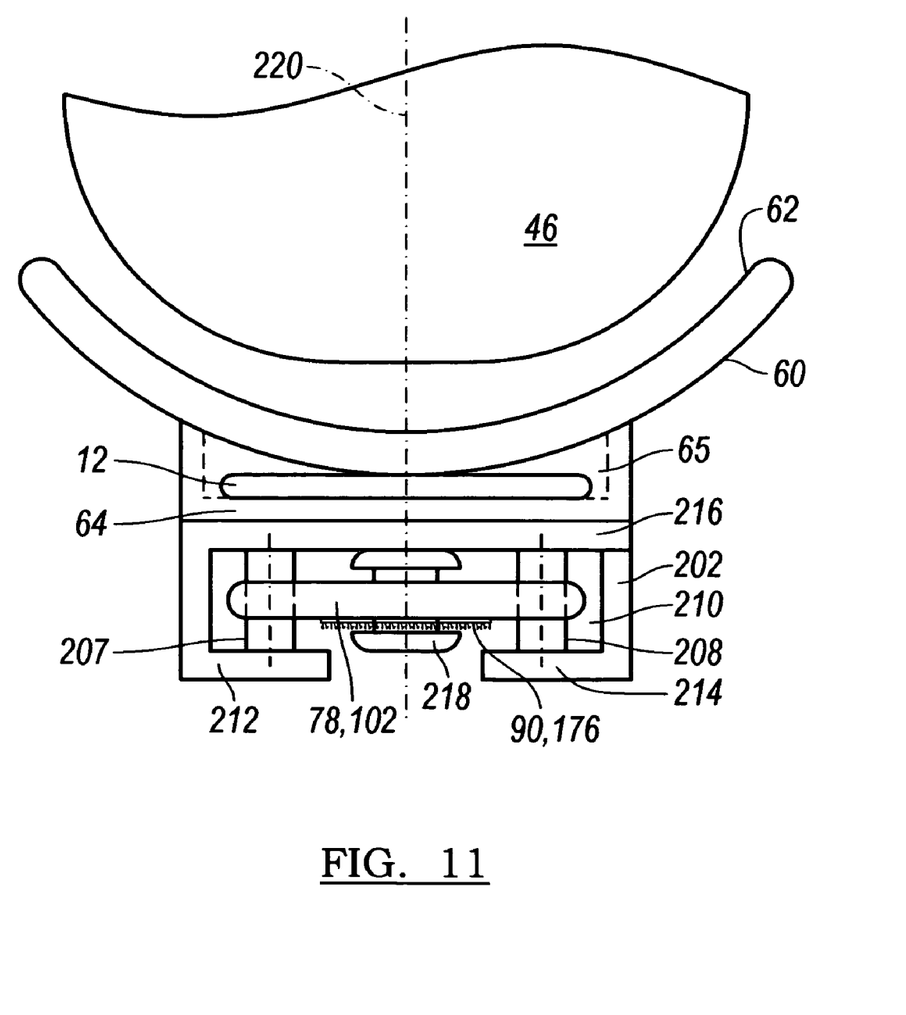
FIG. 11 is a cross sectional top view taken at plane 11-11 of FIG. 10 showing the support member of the extension segment located in and engaged with a spaced bracket slot to allow the extension support member to be aligned relative to the ankle and foot segment along a reference axis.

Referring to FIGS. 10 and 11, the ankle and foot segment of FIG. 1 includes soft material 200 for wrapping the foot supported in the ankle and foot segment 11. The upper portion 66 of the ankle support member 12 is shown inserted in and secured to the channel 65 at the back of the calf support pad 60. The interchangeable support members 78, 102 of the extended upper calf support extension segment 76 or the leg extension segment 100, respectively, depending on which of these is being used to increase the length of the ankle and foot segment 11, is shown inserted into an alternative bracket 202 (i.e. wider than bracket 68 by having further rearward spaced flanges 212 and 214) which is secured by a screw 204 to the wall 64 of the calf support pad 60.

The screw threads of four adjuster set screws 206-209 engage threaded holes in the respective support member 78, 102. The adjuster set screws 206-209, which are located in the longitudinal slot 210 (being more spacious than slot 69 of bracket 68) formed in the alternative bracket 202, engage by mutual contact the inner surfaces of flanges 212, 214 and the inner surface of the front wall 216 of bracket 202. A screw 218 secured to bracket 202 includes a shank that extends across the width of slot 210 and provides a surface, which limits the extent to which the corresponding support member 78, 102 can travel in the slot 210.

As FIG. 11 illustrates, when set screws 206-209 are adjusted such that the corresponding support member, either 78 or 102, is substantially parallel to the slot 210, flanges 212, 214 and wall 216 of bracket 202. As a result, the corresponding support member 78, 102 and the respective support pad(s) 80, 108, 160 is/are aligned with a reference axis, preferably a forward facing, longitudinal axis 220 normal to a plane of the ankle support member 12.

Figure 12:
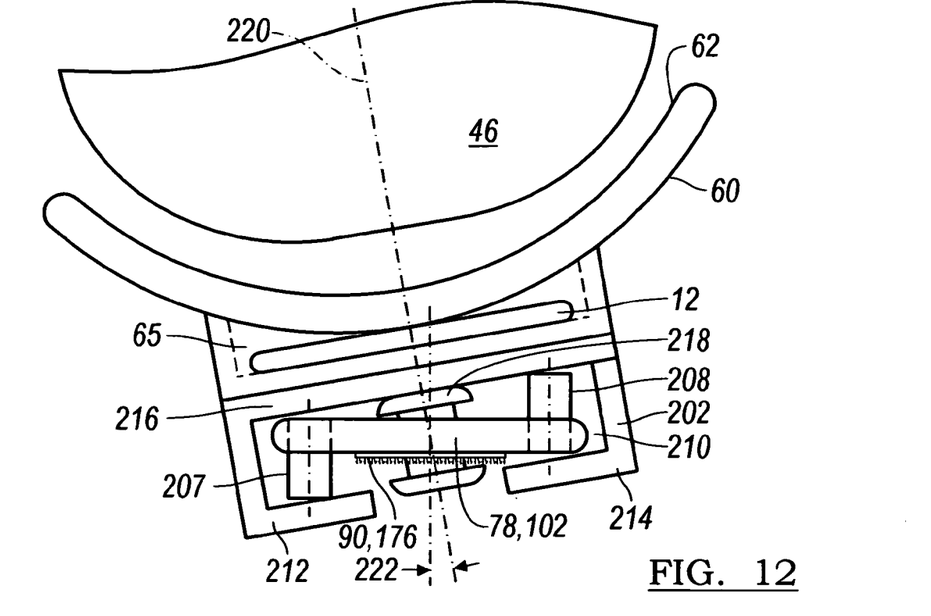
FIG. 12 is a cross sectional top view taken at plane 11-11 of FIG. 10 showing the upper support member of the extension segment rotated with respect to the ankle and foot segment and the reference axis.

As FIG. 12 illustrates, when set screws 206, 207 are adjusted such that the space in slot 210 at the left-hand side of axis 220 between the corresponding support member 78, 102 (but most often the upper leg support member 102 of the leg extension segment 100) and flange 212 is greater than the space between the support member and the front wall 216, and set screws 208, 209 are adjusted such that the space in slot 210 at the right-hand side of axis 220 between the corresponding support member 78, 102 and flange 214 is less than the space between the support member and the front wall 216, the support member 78, 102 and the corresponding support pad (s) 80, 108, 160 of the respective extension segment 76, 100 is/are turned leftward at an angle 222 with respect to reference axis 220.

Figure 13:
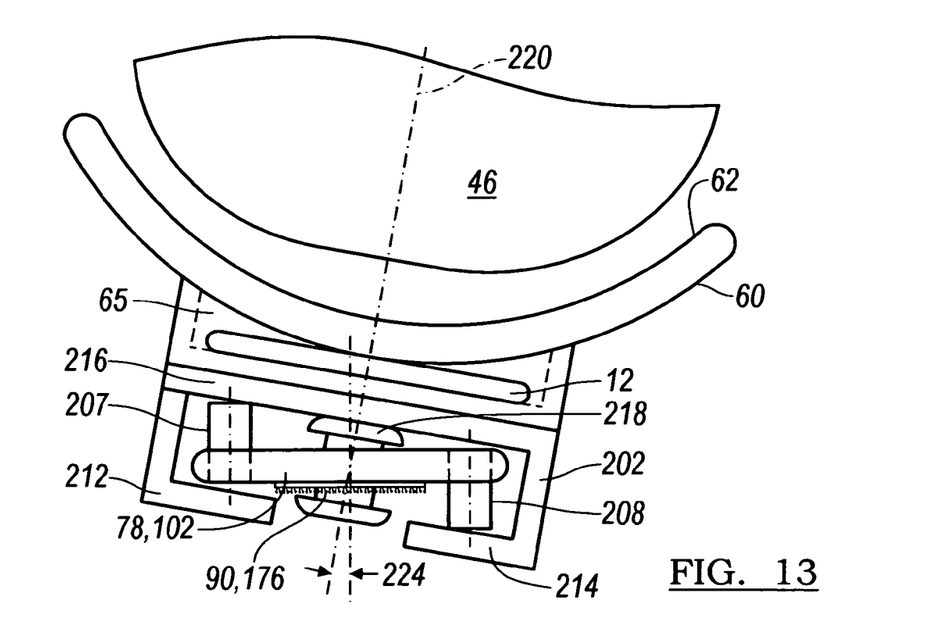
FIG. 13 is a cross sectional top view taken at plane 11-11 of FIG. 10 showing the upper support member of the extension segment rotated in a direction opposite to that of FIG. 12.

As FIG. 13 illustrates, when set screws 206, 207 are adjusted such that the space in slot 210 at the left-hand side of axis 220 between the corresponding support member 78, 102 (but again, most often the upper leg support member 102 of the leg extension segment 100) and flange 212 is less than the space between the support member and the front wall 216, and set screws 208, 209 are adjusted such that the space in slot 210 at the right-hand side of axis 220 between the corresponding support member 78, 102 and flange 214 is greater than the space between the support member and the front wall 216, the support member 78, 102 and the corresponding support pad (s) 80, 108, 160 of the respective extension segment is/are turned rightward, in the opposite direction from that of FIG. 12, at an angle 224 with respect to the reference axis 220.

Notably, the ankle support member 12 and its support pad 60 remain facing forward and aligned with axis 220 regardless of whether support member 78 or 102 is turned askew of axis 220 by adjusting the set screws 206-209. This way, angular adjustability of the extension segment 76, 100 (but most often the leg extension segment 100) with respect to a longitudinal reference axis 220 and the ankle and foot segment 11 of the orthotic, allows for easy and quick adjustment of segment 11 relative to the other segment 76 or 100 to accommodate and progressively urge correction of anomalies associated with soft tissue injuries, particularly about the knee joint during ongoing therapy.

Instead of using set screws 206-209, the angular disposition of the support member 78, 102 with respect to reference axis 220 can be adjusted using shims of variable thickness located in the slot 210 on both side of reference axis 220 to adjust the space between the corresponding support member 78, 102, flanges 212, 214 and the front wall 216 of alternate bracket 202.

Alternatively, the inner surfaces of the front wall 216 and flanges 212, 214 can be inclined with respect to reference axis 220, rather than being normal to the axis 220, to provide a permanent desired angular disposition of the corresponding support member 78, 102 with respect to the reference axis 220.

It should be noted that the present invention can be practiced on limbs other than the leg and foot as specifically illustrated and described, without departing from its spirit or scope. It is intended that all such modifications and alterations be included insofar as they are consistent with the objectives and spirit of the invention.

What is claimed is:

1. An orthotic device for supporting a jointed limb of a human body, comprising:
    a first segment including a first support member that extends along a posterior portion of the limb, a first support pad secured to the first support member, and a channel slot extending along the first support member; and
    an extension segment including a second support member that extends along the posterior portion of the limb and a second support pad secured to the second support member, the extension support member being coupled to the first segment by entering and engaging the channel slot, wherein the extension segment further includes:
    a third support pad located posterior to the limb and at a higher elevation than the second support pad;
    a third support member secured to the third support pad and extending along a posterior portion of the limb; and
    a first connection for securing the second support member and the third support member, wherein the first connection provides an adjustable range of angular motion between the second support member and the third support member about a first axis.

2. The orthotic device of claim 1, wherein the second support member is adjustable into and out of alignment with a longitudinal reference axis.

3. The orthotic device of claim 1, further comprising:
    adjuster screws located in and engaging the slot, the adjuster screws being threadably attached to the second support member for adjusting an angular disposition of the second support member with respect to a longitudinal reference axis.

4. The orthotic device of claim 1, wherein the first connection includes:
    a first surface formed on the third support member and having an arcuate shape centered at the first axis;
    a second surface formed on the second member, overlapping the first surface, and having an arcuate shape centered at the first axis; and
    an attachment for permitting the third support member and the second support member to rotate about the first axis, and for mutually securing the third support member and the second support member.

5. The orthotic device of claim 4, wherein:
    the first segment further includes a lower member extending along an underside of a foot and around a posterior portion of a heel and an ankle; and
    the orthotic device further comprises a second connection that joins the lower member and the first support member and provides an adjustable range of angular motion between the lower member and the first member about a lateral axis.

6. The orthotic device of claim 4, wherein the first segment further comprises a lower member that extends along an underside of a foot and around a posterior portion of a heel and an ankle; and
    the orthotic device further comprises a second connection that includes an arcuate shape centered at a second axis, and an attachment for permitting the first support member and the lower member to rotate about the second axis, and for mutually securing the first support member and the lower member.

7. An orthotic device for supporting a leg of a human body, comprising:
    a foot support member that extends along an underside of a foot and around a posterior portion of a heel;
    an ankle support member attached to the foot support member and extending along a posterior portion of an ankle;
    a first support pad secured to the ankle support member and extending along a lower posterior portion of a calf of the leg;
    a first attachment that joins the foot support member and the ankle support member and provides an adjustable range of angular motion between the foot support member and the ankle support member about a first axis;
    a lower leg support member extending along an upper posterior portion of the calf of the leg;
    a second support pad secured to the lower leg support member and extending along the upper posterior portion of the calf;
    an upper leg support member extending along a posterior portion of a thigh of the leg and pivotally secured to the second support member,
    a third support pad secured to the upper leg support member and extending along the posterior portion of the thigh; and
    a bracket located posterior to the leg and including a slot that is able to couple mutually the ankle support member and the lower leg member when the lower leg support member enters and engages the slot, adjuster screws located in and engaging the slot, the adjuster screws being threadably attached to the lower leg support member for adjusting an angular disposition of the lower leg support member with respect to a longitudinal reference axis.

8. The orthotic device of claim 7, wherein the lower leg support member is adjustable into and out of alignment with the longitudinal reference axis.

9. The orthotic device of claim 7, wherein the orthotic device further comprises:
    a first attachment that includes a first surface formed on the foot support member and having an arcuate shape centered at the first axis, a second surface formed on the ankle support member, overlapping the first surface, and having an arcuate shape centered at the first axis, and a first connection for permitting the foot support member and the ankle support member to rotate about the first axis, and for mutually securing the foot support member and the ankle support member; and a second attachment that includes a third surface formed on the lower leg support member and having an arcuate shape centered at a second axis, a fourth surface formed on the upper leg support member, overlapping the first surface, and having an arcuate shape centered at the second axis, and a second connection for permitting the lower leg support member and the upper leg support member to rotate about the second axis, and for mutually securing the lower leg support member and the upper leg support member.

10. An orthotic device for supporting a leg of a human body, comprising:

a foot support member that extends along an underside of a foot and around a posterior portion of a heel;

an ankle support member extending from the foot support member along a posterior portion of the ankle along a longitudinal reference axis;

a first support pad secured to the ankle support member and extending along a posterior portion of a calf of the leg;

a connection that joins the foot support member and the ankle support member and provides an adjustable range of angular motion between the foot support member and the ankle support member about a lateral axis;

a lower leg support member extending along the posterior portion of the calf;

a second support pad secured to the lower leg support member and extending along the posterior portion of the calf; and a channel slot secured to the ankle support member, the lower leg support member being coupled to the ankle support member by entering and engaging the slot, the lower leg support member being adjustable into and out of alignment with the reference axis by adjuster screws.

11. The orthotic device of claim 10, wherein the adjuster screws are attached to the lower leg support member and engage the slot for adjusting an angular disposition of the lower leg support member with respect to the reference axis.

12. The orthotic device of claim 10, wherein the connection includes a first surface formed on the ankle support member and having an arcuate shape centered at the lateral axis, a second surface formed on the ankle support member, overlapping the first surface, and having an arcuate shape centered at the lateral axis, and an attachment for permitting the foot support member and the ankle support member to rotate about the lateral axis, and for mutually securing the foot support member and the ankle support member.

\* \* \* \* \*